(12) United States Patent
Kam et al.

(10) Patent No.: US 12,310,838 B2
(45) Date of Patent: May 27, 2025

(54) SYSTEM AND METHOD FOR PREPARING A SOFT TISSUE GRAFT

(71) Applicant: CONMED CORPORATION, Utica, NY (US)

(72) Inventors: Andrew Kam, Odessa, FL (US); Giuseppe Lombardo, New Port Richey, FL (US)

(73) Assignee: CONMED CORPORATION, Utica, NY (US)

( * ) Notice: Subject to any disclaimer, the term of this patent is extended or adjusted under 35 U.S.C. 154(b) by 81 days.

(21) Appl. No.: 18/186,251

(22) Filed: Mar. 20, 2023

(65) Prior Publication Data

US 2023/0293285 A1  Sep. 21, 2023

Related U.S. Application Data

(62) Division of application No. 16/647,571, filed as application No. PCT/US2018/048214 on Aug. 28, 2018, now Pat. No. 11,628,057.

(60) Provisional application No. 62/718,715, filed on Aug. 14, 2018, provisional application No. 62/650,379, filed on Mar. 30, 2018, provisional application No. 62/550,840, filed on Aug. 28, 2017.

(51) Int. Cl.
*A61F 2/08* (2006.01)

(52) U.S. Cl.
CPC .... *A61F 2/0805* (2013.01); *A61F 2220/0075* (2013.01); *A61F 2240/001* (2013.01)

(58) Field of Classification Search
CPC ............ A61F 2/0805; A61F 2220/0075; A61F 2240/001
See application file for complete search history.

(56) References Cited

U.S. PATENT DOCUMENTS

| 12,042,373 B1* | 7/2024 | Sundholm | ............... A61L 27/12 |
| 2003/0036770 A1* | 2/2003 | Markman | .......... A61B 17/3468 |
| | | | 606/187 |
| 2004/0204722 A1 | 10/2004 | Sikora et al. | |
| 2006/0259076 A1 | 11/2006 | Burkhart et al. | |

(Continued)

FOREIGN PATENT DOCUMENTS

EP    2663242 A1    11/2013

OTHER PUBLICATIONS

CN Office Action, Application No. 202111423298.3, dated Aug. 29, 2023, pp. 1-7.

(Continued)

*Primary Examiner* — Suzette J Gherbi
(74) *Attorney, Agent, or Firm* — Bond, Schoeneck & King, PLLC; Frederick J.M. Price

(57) ABSTRACT

A system and method for loading a suture construct on a soft tissue graft with a graft assembly. The graft assembly includes a suture construct having a closed end and an open end; a first tail of suture and a second tail of suture positioned adjacent to the open end; a first closed loop positioned at the closed end formed from the first and second tails of suture; a first splice formed by the first tail in the second tail between the closed loop and the open end; a second closed loop formed from the first and second tails of suture between the splice and the open end; and a second splice formed by the first tail in the second tail between the second closed loop and the open end.

7 Claims, 11 Drawing Sheets

(56) References Cited

U.S. PATENT DOCUMENTS

| | | | |
|---|---|---|---|
| 2011/0208239 A1* | 8/2011 | Stone | A61B 17/06004 |
| | | | 606/228 |
| 2015/0351739 A1* | 12/2015 | Napolitano | D07B 1/18 |
| | | | 606/228 |
| 2016/0008123 A1 | 1/2016 | Woodruff et al. | |
| 2016/0220242 A1* | 8/2016 | Dougherty | A61B 17/0401 |
| 2017/0128215 A1 | 5/2017 | Denham | |
| 2017/0172725 A1* | 6/2017 | Gustafson | A61F 2/08 |
| 2020/0205805 A1* | 7/2020 | Marks | A61B 17/1796 |
| 2020/0237521 A1* | 7/2020 | Siegal | A61F 2/4455 |
| 2021/0228202 A1* | 7/2021 | Hernandez | A61B 17/0401 |
| 2022/0000634 A1* | 1/2022 | Cain | A61F 2/447 |

OTHER PUBLICATIONS

CA Office Action, dated May 7, 2024, Application No. 3184686, pp. 1-6.

\* cited by examiner

SYSTEM AND METHOD FOR PREPARING A SOFT TISSUE GRAFT

CROSS-REFERENCE TO RELATED APPLICATIONS

This application is a divisional of U.S. Non-Provisional patent application Ser. No. 16/647,571, filed on Mar. 16, 2020, which claims priority to U.S. Provisional Patent Application Ser. No. 62/550,840, filed on Aug. 28, 2017, and entitled "System for Preparing a Soft Tissue Graft," U.S. Provisional Patent Application Ser. No. 62/650,379, filed on Mar. 30, 2018, and entitled "Device for Increasing Micro-Blood Vessel Circulation and Method of Treatment Using Same," and U.S. Provisional Patent Application Ser. No. 62/718,715, filed on Aug. 14, 2018, and entitled "Graft Preparation System."

BACKGROUND OF THE INVENTION

1. Field of the Invention

The invention relates generally to graft preparation and more particularly, a system and method for loading a suture construct on a soft tissue graft.

2. Description of Related Art

Grafting is a surgical procedure of transferring tissue from one surgical site to another surgical site. Grafting may be used in procedures to repair injuries to the skin, in dental implants, and in ligament repair, such as knee ligament repair, for example. As such, a variety of tissues may be grafted, including, but not limited to skin, bone, and tendons. Further, grafts can be composed of synthetic material or harvested from an individual (either the patient or a donor).

The ability to prepare grafts quickly and securely provides benefits to the surgeon in reducing the overall duration of the surgical procedure. One traditional method for preparing a graft includes whip stitching. Whip stitching is commonly used method for preparing a graft in ligament repair, such as ACL surgery. Further, during the step of harvesting a soft tissue autograft, it is desirable to pass stiches through the end to maintain control and provide counter traction. In both whip stitching and passing stiches during harvesting, the task of stitching the graft is a long and labor intensive process that requires multiple piercings of the graft. Every piercing increases time required to prepare the graft and causes trauma to the graft.

Other methods for preparing the graft have been developed to reduce trauma to the graft. For example, suture constructs having a fixed, central main line ("spine") have been deployed around the graft. The spine was designed to prevent collapsing of the suture construct prior to deployment around the graft. However, the spine limits the radial compression on the graft and reduces the contact area between the graft and the bone tunnel.

Therefore, there is a need for a system and method for graft preparation that reduces the number of piercings of the graft, reduces the time required to prepare the surgical graft, and improves the graft to bone contact.

SUMMARY OF THE INVENTION

The present invention is directed to graft preparation, inter alia, a system and method for loading a suture construct on a soft tissue graft. In one aspect, the present invention is a graft assembly. The graft assembly includes a frame with an opening extending between a proximal end and a distal end. The frame has a wall with a first side extending to a first edge and a second side extending to a second edge. A lumen extends between the first side and the second side and a plurality of channels extend through the wall between the first edge and the second edge. The graft assembly also includes a transverse hole extending through the proximal end of the frame and a pin removably inserted into the transverse hole.

In another aspect, the graft assembly includes a suture construct having a closed end and an open end with a first tail of suture and a second tail of suture at the open end. The suture construct also has a first closed loop at the closed end formed from the first and second tails of suture. A first splice is formed by the first tail in the second tail between the closed loop and the open end. A second closed loop is formed from the first and second tails of suture between the splice and the open end and a second splice is formed by the first tail in the second tail between the second closed loop and the open end.

In yet another aspect, the graft assembly includes a frame having a first side at a proximal end and a second side at a distal end with a lumen extending through the frame between the proximal end and the distal end. The graft assembly also includes a sliding spacer, which is removably insertable into the lumen. The sliding spacer has at least two spaced fingers extending from its distal end. When the sliding spacer is inserted into the lumen, there is a channel between the fingers.

According to another aspect, the present invention is a method for preparing a graft. The method comprises the steps of: (i) providing a frame having a proximal end and a distal end, a lumen extending through the frame from the proximal end to the distal end, a plurality of channels extending along the frame, and a transverse hole extending through the proximal end of the frame; (ii) inserting a pin into the transverse hole; (iii) inserting a graft into the lumen of the frame; and (iv) weaving a length of suture through the channels over the graft.

According to another aspect, the step of (iv) weaving a length of suture through the channels over the graft comprises the step of (v) threading a first tail and a second tail of the length of suture through a proximal end of the graft.

According to another aspect, the method includes the step of: (vi) removing the pin from the transverse hole.

According to yet another aspect, the method includes the step of: (vii) removing the frame from the graft with the woven length of suture from the frame.

According to another aspect, the method includes the step of: (viii) tensioning the first and second tails of suture.

According to another aspect, the step of (viii) tensioning the first and second tails of suture radially compresses the length of suture around the graft.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
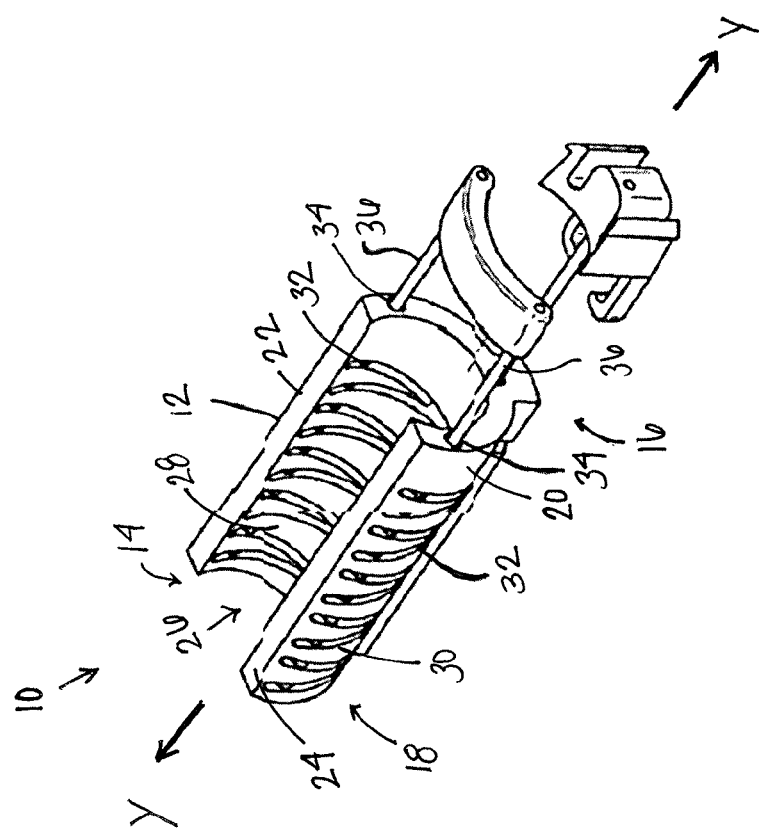
FIG. 1 is a top perspective view schematic representation of a graft assembly in the open, unloaded configuration, according to an embodiment.

Referring now to FIG. 1, there is shown a top perspective view of a graft assembly 10 in the open, unloaded configuration, according to an embodiment. As shown, the graft assembly 10 comprises a frame 12 extending along a central longitudinal y-y axis. The frame 12 has an open side 14 extending along the central longitudinal y-y axis and extends between a proximal end 16 and a distal end 18. In the depicted embodiment, the frame 12 is semi-cylindrical such that the frame 12 comprises a wall 20 extending between a first edge 22 and second edge 24, defining a lumen 26 therebetween. The lumen 26 extends between the first and second edges 22, 24 through the frame 12.

As shown in FIG. 1, the wall 20 has a first side 28 extending to the first edge 22 on one side of the central longitudinal y-y axis and the wall 20 has a second side 30 extending to the second edge 24 on an opposing side of the central longitudinal y-y axis. In the depicted embodiment, first edge 22 and second edge 24 are parallel; however, other configurations of the frame 12 and the edges 22, 24 are contemplated. As also shown, the first and second edges 22, 24 are flat and extend in the same plane.

Still referring to FIG. 1, the wall 20 of the frame 12 comprises a plurality of channels 32 extending between the first edge 22 and the second edge 24. In the depicted embodiment, the channels 32 are paired such that two channels 32 converge near the central longitudinal y-y axis and diverge toward the first and second edges 22, 24. The frame 12 also comprises one or more transverse holes 34 on the proximal end 16 of the frame 12. The transverse holes 34 extend at least partially through the first and second sides 22, 24 of the frame 12. In the depicted embodiment, the transverse holes 34 extend through the first and second sides 22, 24 of the frame 12 to the distal end 18 and past all of the channels 32. The transverse holes 34 are sized and configured to receive pins 36. When the pins 36 are inserted into and extended through the transverse holes 34, the pins 36 retain the open lumen 26 and prevent inadvertent dislodging of the limbs of suture, as described in detail below. One or more pins 36 can be coupled in a variety of arrays and configurations to control the release of suture from the frame 12.

Figure 2:
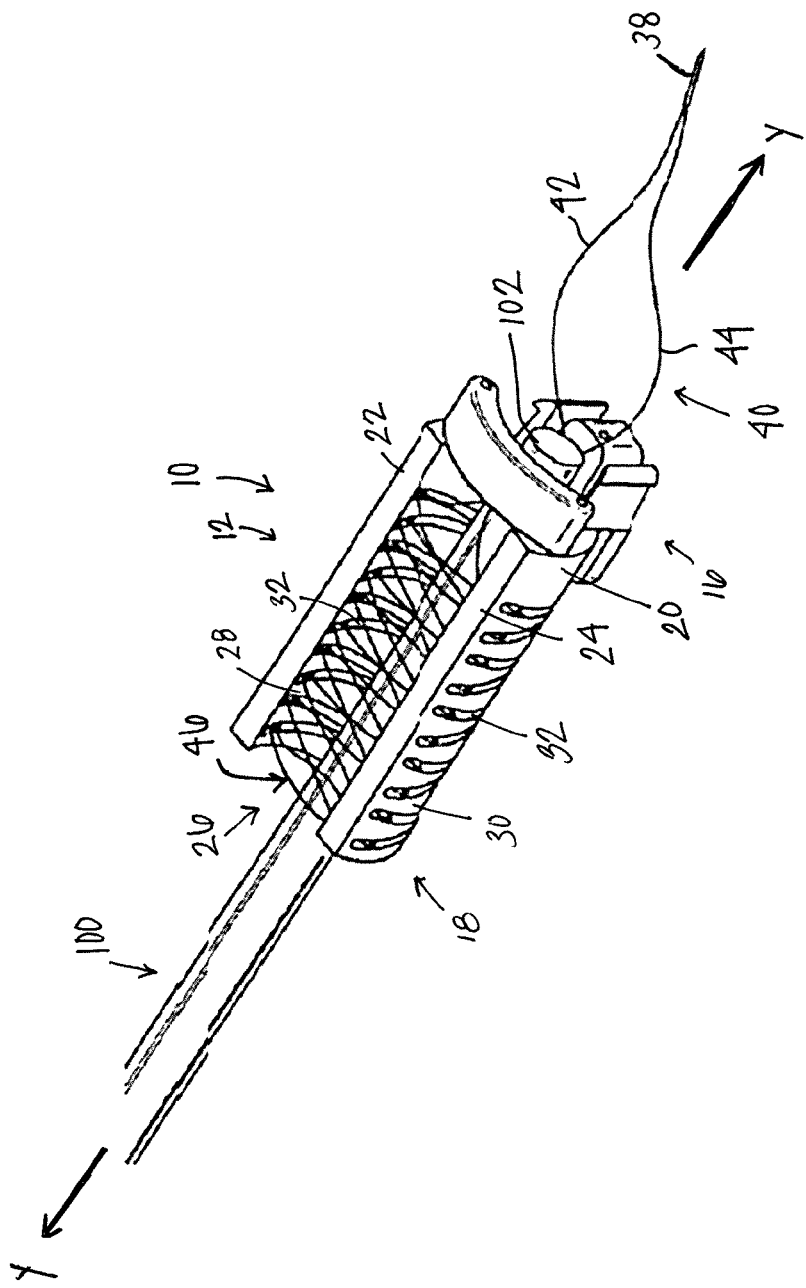
FIG. 2 is a top perspective view schematic representation of a graft assembly in the closed, loaded configuration, according to an embodiment.

Turning to FIG. 2, there is shown a top perspective view schematic representation of a graft assembly 10 in the closed, loaded configuration, according to an embodiment. To achieve the closed, loaded configuration shown in FIG. 2, the pins 36 are first inserted into and extended through the transverse holes 34 on the proximal end 16 of the frame 12. Next, a graft 100 is loaded into the lumen 26 of the frame 12. As shown in FIG. 2, the graft 100 is loaded into the lumen 26 such that at least a proximal end 102 of the graft 100 extends beyond the wall 20 at the proximal end 16 of the frame 12.

Still referring to FIG. 2, after a graft 100 is inserted in to the lumen 26, a needle 38 is coupled to the proximal end 16 of the frame 12. In the depicted embodiment, the needle 38 is secured to the proximal end 16 of the frame 12 via suture 40. The needle 38 is then used to pierce through the graft 100, passing a first tail 42 and a second tail 44 of suture 40 (connected to the needle 38) therethrough. The suture 40 is passed through the graft 100 and through the channels 32. The arrangement or configuration of the channels 32 accepts the suture 40 into an opposing double helical pattern, forming a trap 46. When the trap 46 is formed, as shown in FIG. 2, the first and second tails 42, 44 of suture 40 are cut to remove the needle 38.

To deploy the trap 46 around the graft 100, all but one transverse pin 36 is removed from the frame 12. The trap 46 collapses on the graft 100 as tension is applied to the first and second tails 42, 44 of suture 40. By removing all but one transverse pin 36, the trap 46 collapses on the graft 100 but maintains the gapping or spacing (by the opposing double helical pattern). Once the trap 46 is deployed on the graft 100, the final transverse pin 36 is removed to free the graft 100, in the prepared configuration, from the frame 12.

Figure 3:
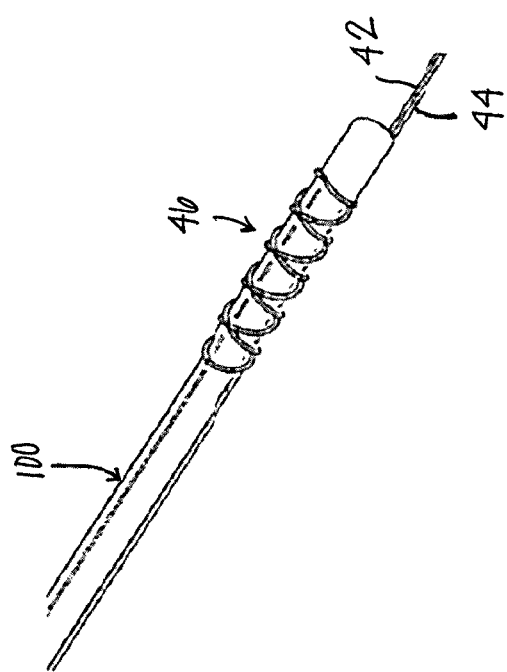
FIG. 3 is a perspective view schematic representation of a graft in the prepared configuration, according to an embodiment.

Referring now to FIG. 3, there is shown the graft 100 in the prepared configuration, according to an embodiment. As shown, the trap 46 is formed on the graft 100 in the opposing double helical pattern. Tension can be applied to the first and second tails 42, 44 of suture 40 to remove any remaining slack between the trap 46 and the graft 100. In the prepared configuration, any additional tension on the first and second tails 42, 44 of suture 40 causes radial compression (by the trap 46) on the graft 100.

Figure 4:
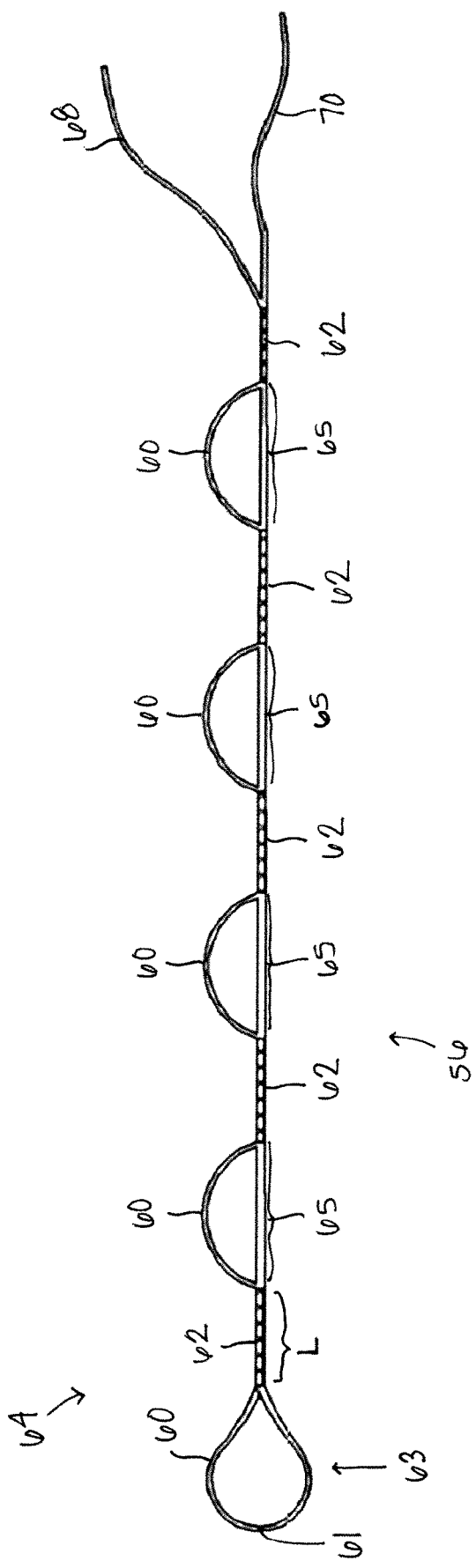
FIG. 4 is a side view schematic representation of a trap of the graft assembly, according to an alternative embodiment.

Turning now to FIGS. 4-7, there are shown perspective views schematic representations of a graft assembly 50, according to an alternative embodiment. Referring now to FIG. 4, there is shown a perspective view schematic representation of a trap (e.g., suture construct) 64 of the graft assembly 50, according to an alternative embodiment. The trap 64 shown in FIG. 4 is a suture construct composed of a single strand of suture 56. In the depicted embodiment, the suture 56 is folded at approximately the midpoint 61 of the suture 56 to form a closed end 63 extending to a first tail 68 and a second tail 70. The first tail 68 is spliced into the second tail 70, splice 62, over a first length L to create a closed loop 60 at the closed end 63.

Still referring to FIG. 4, additional splices 62 are formed by the first tail 68 into the second tail 70 in a series along the second tail 70, as shown. The number of splices 62 formed in the second tail 70 depends on a variety of factors, such as the size of the graft 100 and the surgical site for implantation of the graft 100, for example. In the depicted embodiment, there are gaps 65 between the splices 62, each of which forms a closed loop 60. Thus, there can be multiple closed loops 60 along the length of the graft 100.

Figure 5:
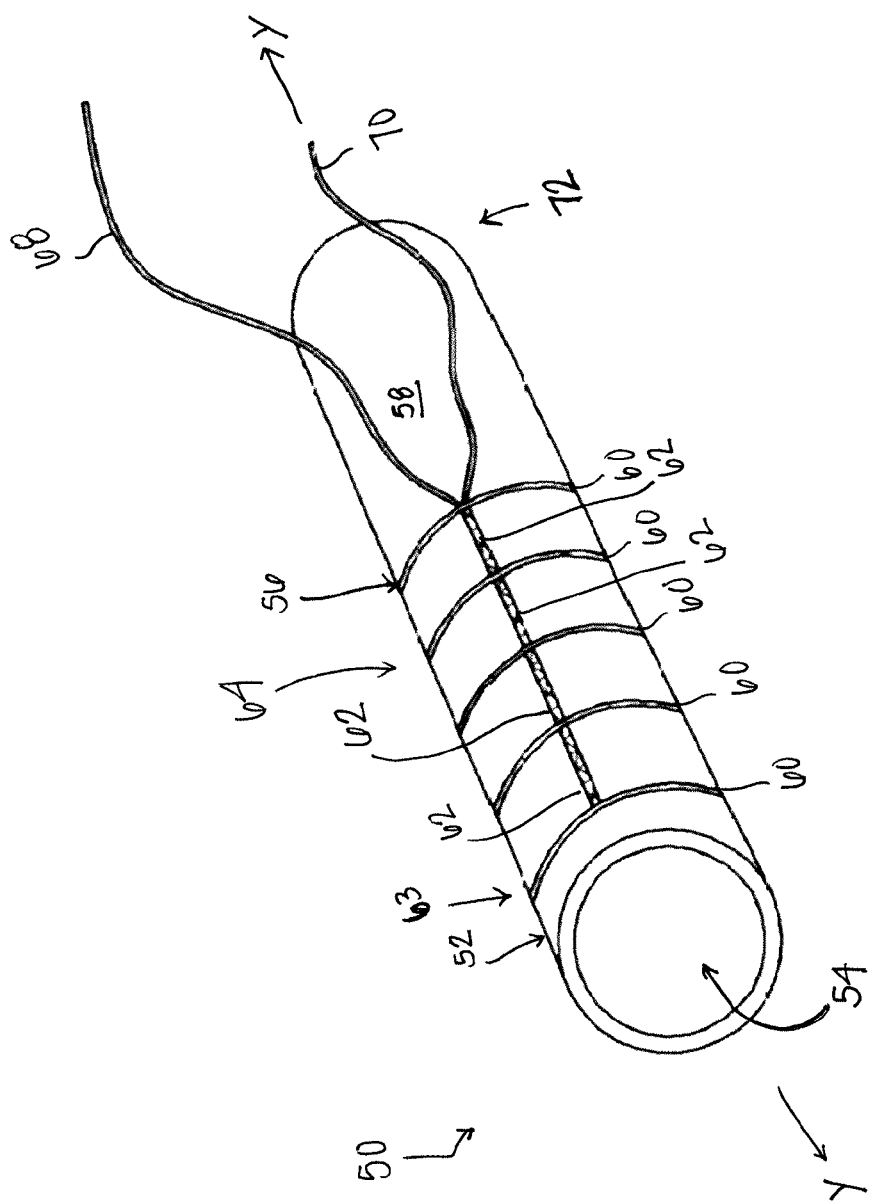
FIG. 5 is a perspective view schematic representation of a graft assembly in the closed, unloaded configuration, according to an alternative embodiment.

Turning now to FIG. 5, there is shown a perspective view of the graft assembly 50 in the closed, unloaded configuration, according to an alternative embodiment. The graft assembly 50 of FIG. 5 includes a hollow tube 52 extending along a central longitudinal y-y axis with an inner lumen 54. In the closed, unloaded configuration, the trap 64 (FIG. 4) is loaded onto the outer surface 58 of the hollow tube 52. In the depicted embodiment, the hollow tube 52 is inserted through each of the closed loops 60 with the splices 62 extending along the length of the hollow tube 52 of the trap 64. The formation of the closed loops 60 through multiple splices 62 functions to maintain the spacing of the closed loops 60. The splices 52 prevent collapsing of the trap 64 when tensioned around the graft 100, which can improve the contact between the graft 100 and a bone, as compared to other graft preparation methods. The splices 52 eliminate the need for a stationary or fixed spine extending along the length of conventional traps. In the embodiment depicted in FIGS. 5-7, when the trap 64 is loaded onto the hollow tube 52, the first and second tails 68, 70 of suture 56 extend from the splices 52 toward a proximal end 72 of the hollow tube 52.

Figure 6:
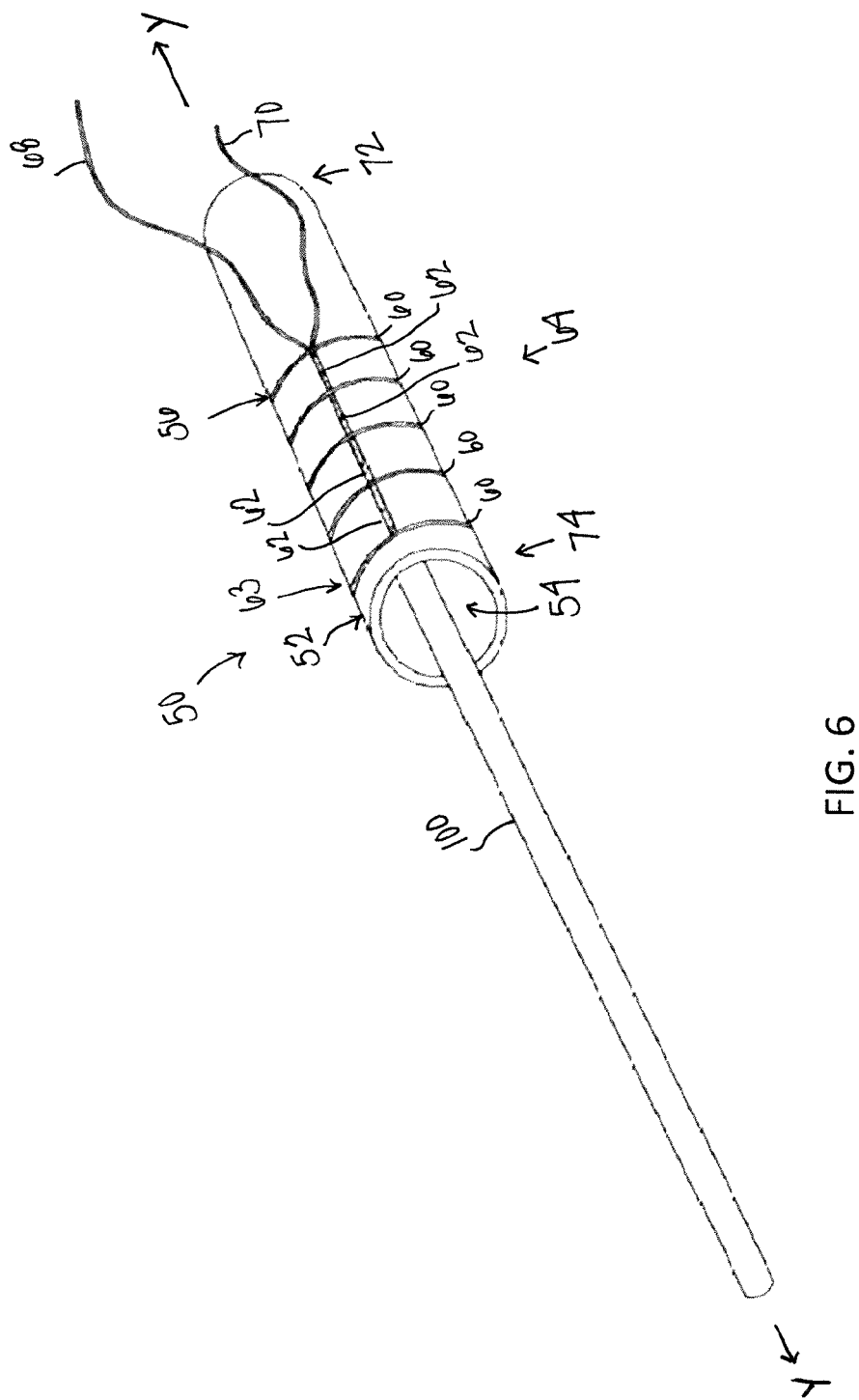
FIG. 6 is a perspective view schematic representation of a graft assembly in the closed, loaded configuration, according to an alternative embodiment.

Referring now to FIG. 6, there is shown a perspective view schematic representation of the graft assembly 50 in the closed, loaded configuration, according to an alternative embodiment. As shown in FIG. 6, a graft 100 is inserted into the inner lumen 54 of the hollow tube 54 through its distal end 74. The graft 100 can be any type of graft 100, including, but not limited to the soft tissue graft 100 shown in FIG. 3 and described above. To deploy the trap 64 around the graft 100, the hollow tube 52 is removed by pulling it back through the closed loops 60 of the trap 64.

Figure 7:
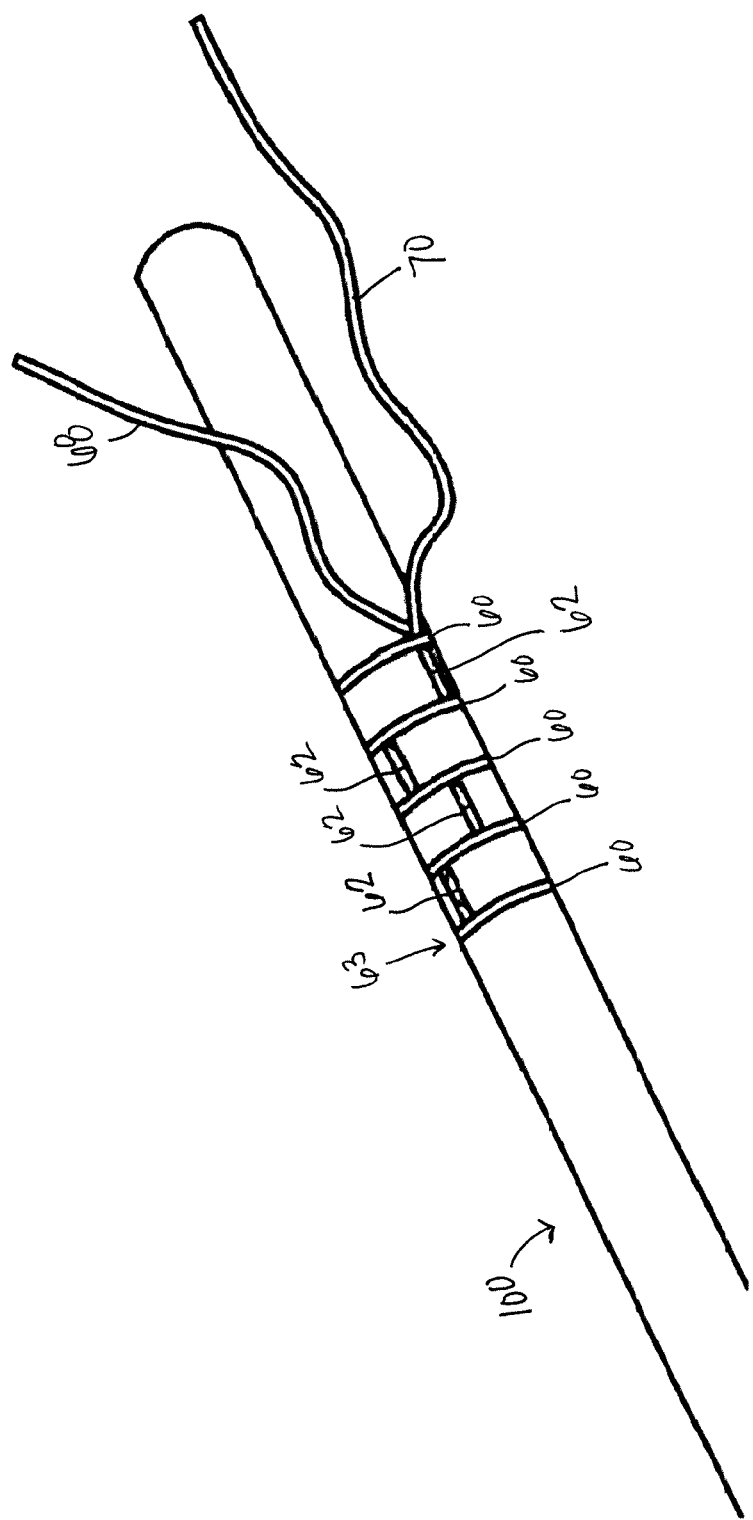
FIG. 7 is a perspective view schematic representation of a graft in the prepared configuration, according to an alternative embodiment.

Turning now to FIG. 7, there is shown a perspective view schematic representation of the graft 100 in the prepared configuration, according to an alternative embodiment. In the depicted embodiment, the hollow tube 52 has been pulled out from the closed loops 60 of the trap 64, leaving the trap 64 surrounding the graft. Once the trap 64 is around the graft 100, the first and second tails 68, 70 of suture 56 are pulled to tighten or otherwise compress the trap 64 around the graft 100, resulting in the prepared configuration shown in FIG. 7. As the first and second tails 68, 70 are tensioned, the splices 62 are tightened. As the slack in the splices 62 is reduced, the splices 62 may rotate (at least partially) around the graft 100, as shown in FIG. 7.

Figure 8:
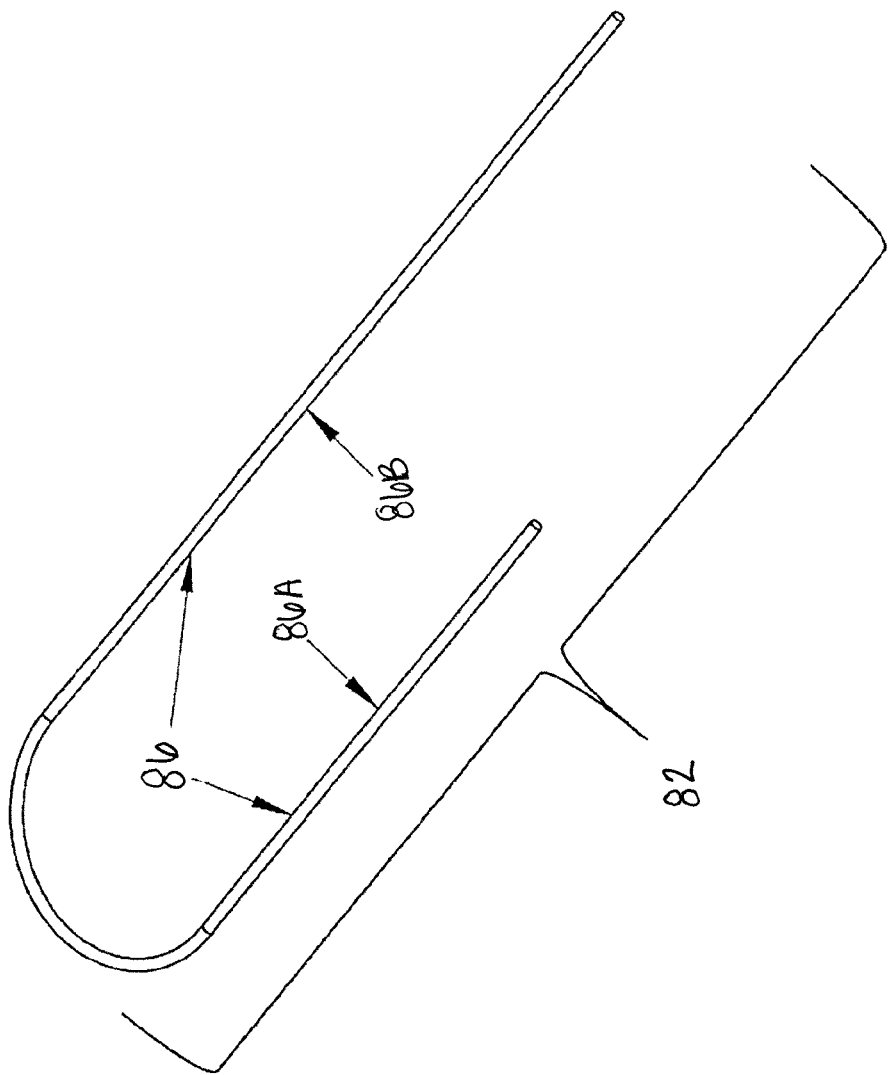
FIG. 8 is a top perspective view schematic representation of a length of suture, according to an alternative embodiment.
Figure 9:
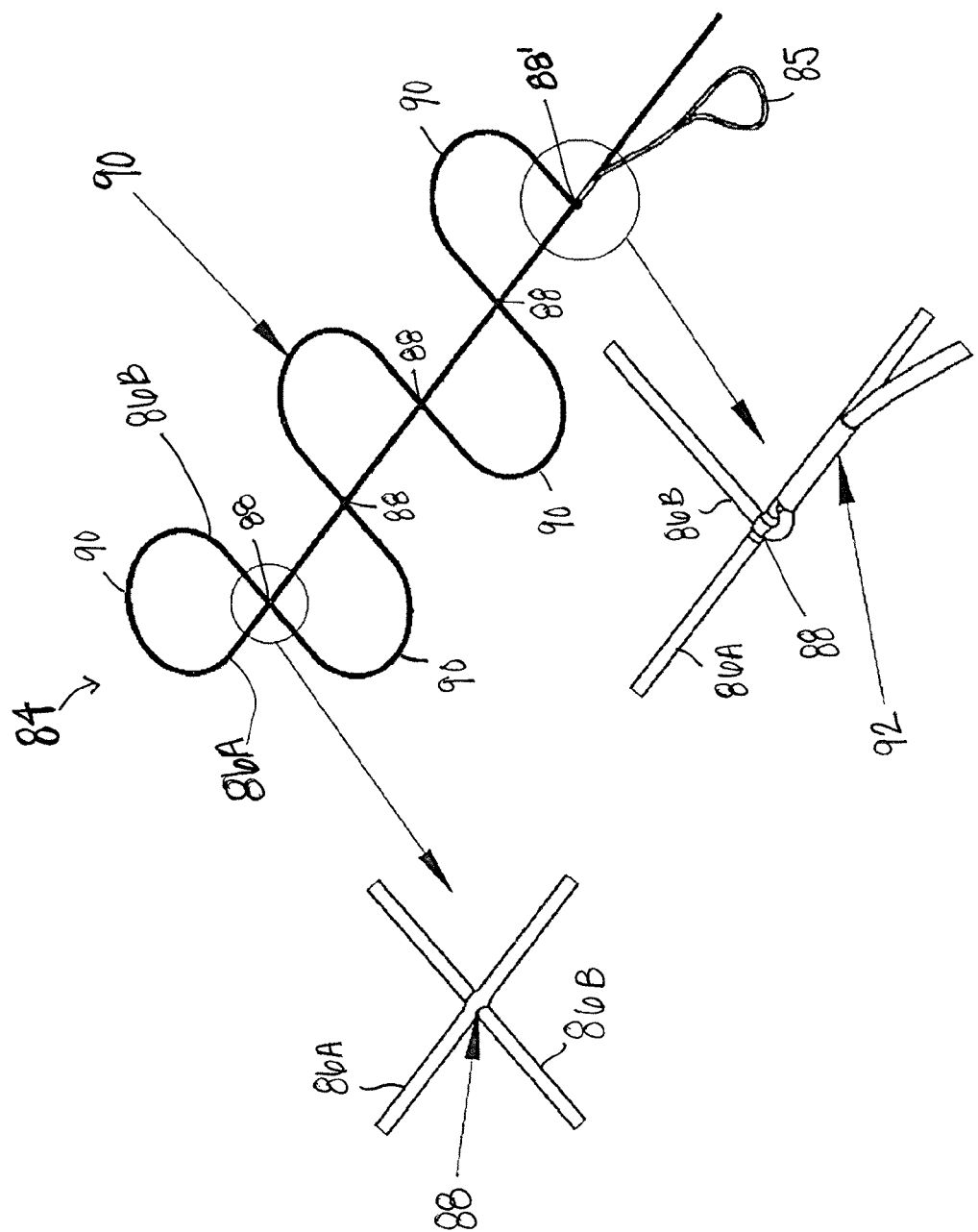
FIG. 9 is a top perspective view schematic representation of a suture construct, according to an alternative embodiment.

Turning now to FIGS. 8-11, there are shown perspective views schematic representations of a graft assembly 80, according to an alternative embodiment. Referring now to FIG. 8, there is shown a top perspective view schematic representation of a continuous length of suture 82 used to create the trap (e.g., suture construct) 84 (shown in FIG. 9) of the graft assembly 80, according to an alternative embodiment. The trap 84 (FIG. 9) is created by folding the length of suture 82 (i.e., into a "U" shape) forming two limbs 86, as shown in FIG. 8. Of the two limbs 86, there is a post, first limb 86A and a sliding, second limb 86B. The sliding, second limb 86B is pierced and passed through the post, first limb 86A at a series of passing locations 88, creating a series of adjustable loops 90 along the post, first limb 86A. Adjacent a last passing location 88', the sliding, second limb 86B is passed through a splice 92 in the post, first limb 86A, as shown in FIG. 9. In the depicted embodiment, the sliding, second limb 86B comprises a looped end 85, which extends from the splice 92.

Figure 10:
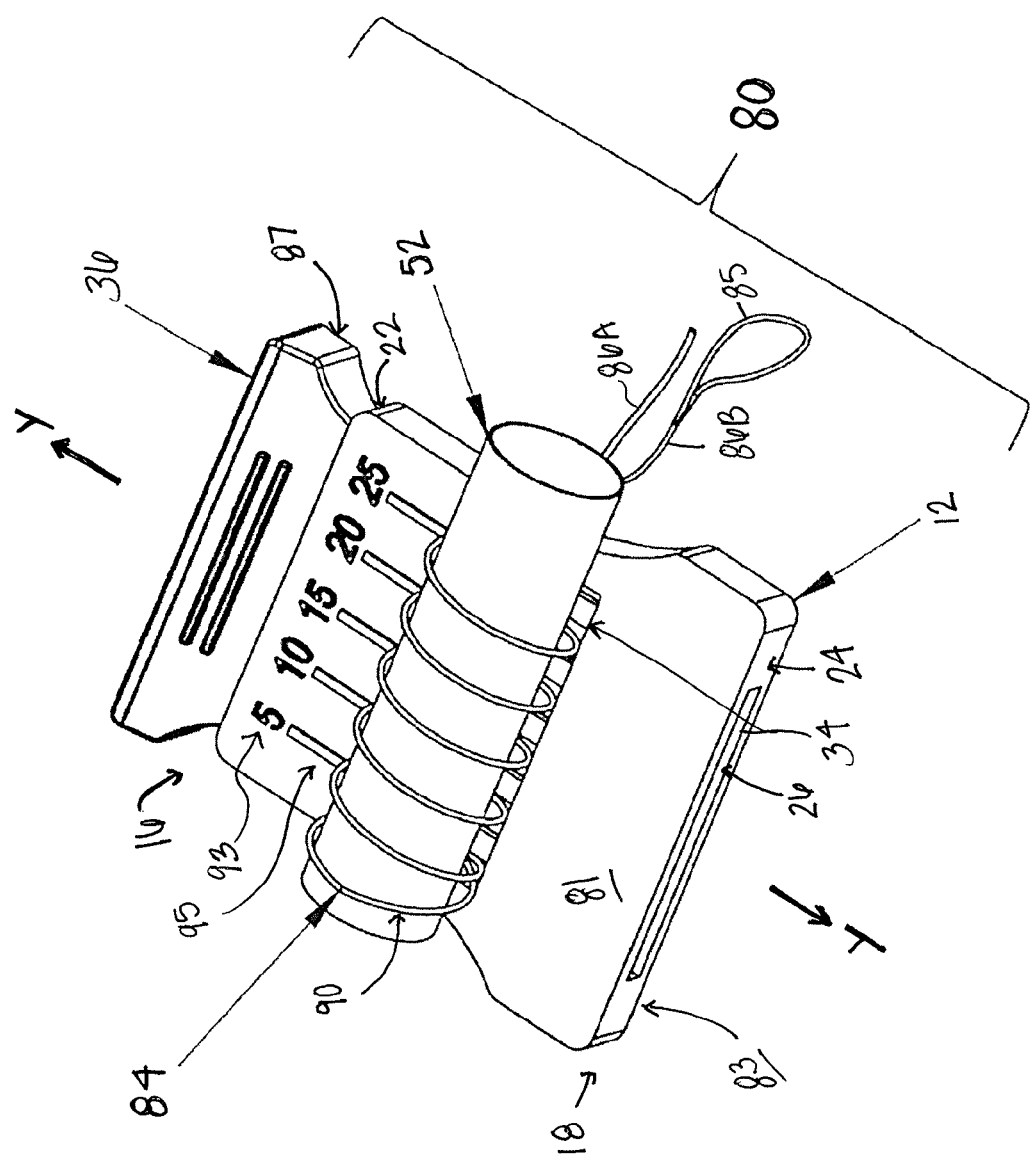
FIG. 10 is a top perspective view schematic representation of a graft assembly in the closed, loaded configuration, according to an alternative embodiment.
Figure 11:
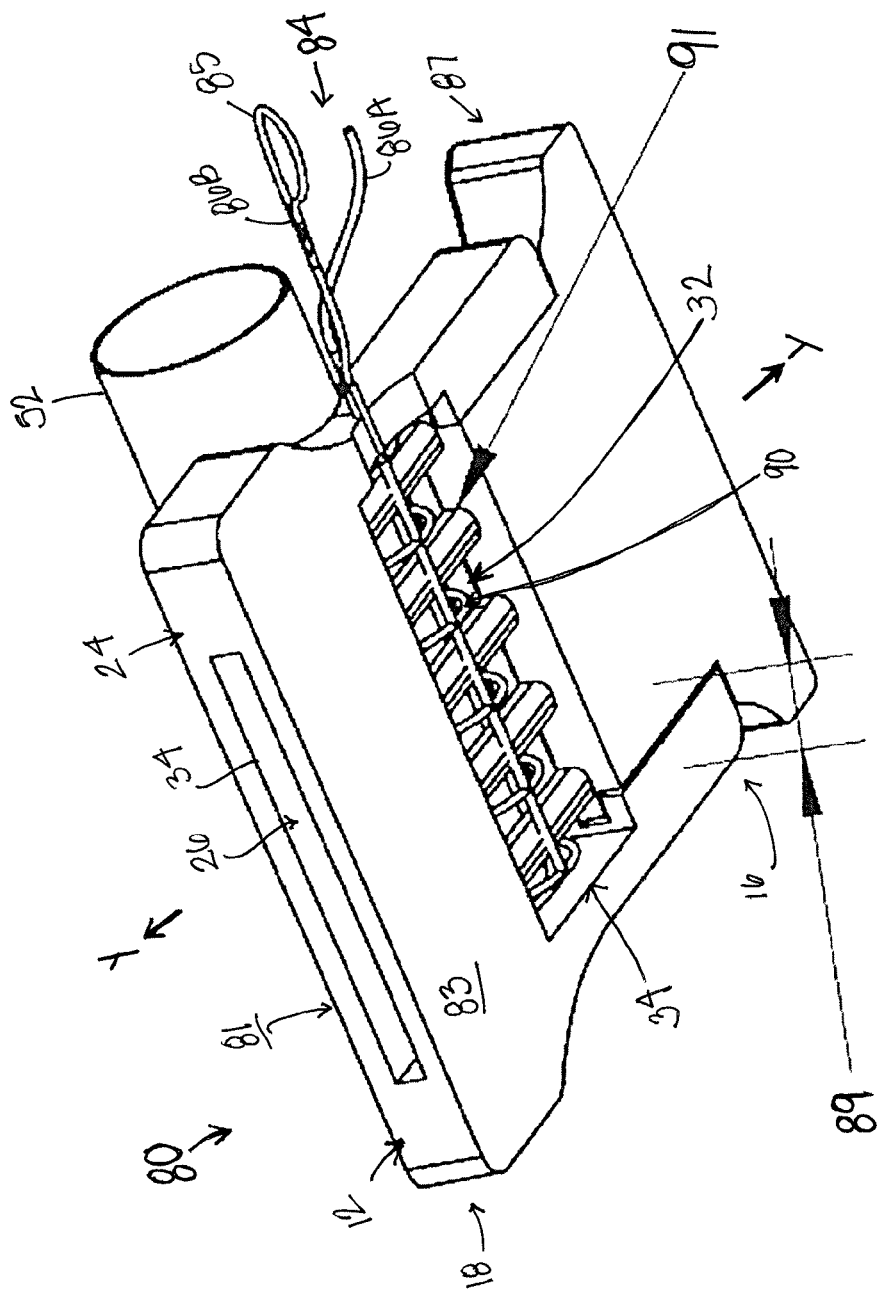
FIG. 11 is a bottom perspective view schematic representation of a graft assembly in the closed, loaded configuration, according to an alternative embodiment.

FIGS. 10-11 show top and bottom perspective views schematic representations of the trap 84 (in FIG. 9) loaded onto the graft assembly 80, according to an alternative embodiment. Similar to the embodiment of the graft assembly 10 in FIGS. 1-2, the graft assembly 80 in FIGS. 10-11 comprises a frame 12 extending along a central longitudinal y-y axis and between a proximal end 16 and a distal end 18. In the depicted embodiment, the frame 12 is substantially rectangular with a first side 22 at the proximal end 16 and a second side 24 at the distal end 18. A slot 26 extends from the second side 24 to a lumen 34 within the frame 12. In the depicted embodiment, the lumen 34 extends through a top side 81 and a bottom side 83 of the frame 12. The lumen 34 is sized or otherwise configured to receive a sliding spacer 36, which is comparable to the pins 36 of the embodiment of the graft assembly 100 shown in FIG. 1.

Still referring to FIGS. 10-11, the sliding spacer 36 is slidable within the lumen 34 of the frame 12. In the depicted embodiment, the sliding spacer 36 comprises a handle end 87, which is wider than the lumen 34 such that the handle end 87 facilitates proper placement of the sliding spacer 36 within the lumen 34. The sliding spacer 36 also comprises a pronged distal end with a plurality of fingers (e.g., rods or prongs) 91 connected thereto. When the graft assembly 80 is in the closed, loaded configuration, as shown in FIGS. 10-11, the sliding spacer 36 is inserted within the lumen 26 such that the fingers 91 extend across the lumen 34, creating a channel 32 between the fingers 91. In the depicted embodiment, the fingers 91 extend parallel to the central longitudinal y-y axis in the lumen 34.

To load the graft assembly 80, each loop 90 of the trap 84 is inserted through a channel 32 such that the post, first limb 86A extends on the bottom side 83 of the frame 12, maintaining the pitch 89 of the trap 84. As shown in FIGS. 10-11, the loops 90 extend up through the channels 32 and a hollow tube 52 is passed through the loops 90 on the top side 81 of the frame 12. When the trap 84 is loaded on the hollow tube 52, the trap 84 is in a collapsible helical shape. As shown, the hollow tube 52 extends transversely over the channels 32 (perpendicular to the central longitudinal y-y axis).

Similar to the embodiment shown in FIGS. 4-7, a graft (not shown) is inserted into the hollow tube 52 at a desired distance. In the depicted embodiment, the top side 81 of the graft assembly 80 has graduations 95 with indicators 93 denoting the distance the graft (not shown) has traveled within the hollow tube 52. Once the graft (not shown) is at a desirable position within the hollow tube 52, the hollow tube 52 is removed, leaving the graft (not shown) within the trap 84 on the top side 81 of the frame 12. Traction is then applied to the looped end 85 of the sliding, second limb 86B. The traction causes the helical shaped trap 84 to collapse radially around the graft (not shown). After the trap 84 is radially collapsed, the sliding spacer 36 is removed from the lumen 34 (and frame 12), releasing the trap 84. Additional tension can then be applied to completely collapse the trap 84 on the graft (not shown). The trap 84 shown in FIG. 9 reduced frictional resistance during the act of collapsing the trap 84 on the graft (not shown). The reduction in frictional resistance is due to the low sliding resistance of the sliding, second limb 86B passing through the post, first limb 86A at the passing locations 88. The terminal splice 92 resists loosening and maintains residual tension on the trap 84 after the tension on the sliding, second limb 86B is released.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A graft assembly, comprising:
   a suture construct having a closed end and an open end;
   a first tail of suture and a second tail of suture positioned adjacent to the open end;
   a first closed loop positioned at the closed end formed from the first and second tails of suture;
   a first splice formed to one side of the first closed loop by the first tail extending over a predetermined length of and within the second tail between the closed loop and the open end;
   a second closed loop formed from the first and second tails of suture next to the first splice towards the open end; and
   a second splice formed to one side of the second closed loop by the first tail extending over a predetermined length of and within the second tail towards the open end.

2. The graft assembly of claim 1, further comprising a hollow tube extending through the first closed loop and the second closed loop.

3. The graft assembly of claim 2, wherein the first and second closed loops extend perpendicular to the central longitudinal axis extending through the hollow tube.

4. The graft assembly of claim 2, wherein the hollow tube has an inner lumen extending therethrough.

5. The graft assembly of claim 4, wherein a graft extends at least partially through the inner lumen.

6. The graft assembly of claim 1, wherein the first and second tails of suture are of a single strand of suture.

7. The graft assembly of claim 1, further comprising: a number of additional splices, each additional splice formed by the first tail extending over a predetermined length of and within the second tail towards the open end; and a number of additional closed loops formed by the first and second tails of suture in gaps located between the series of additional splices.

\* \* \* \* \*